United States Patent [19]
Kosuge et al.

[11] Patent Number: 4,801,453
[45] Date of Patent: Jan. 31, 1989

[54] STABILIZED MUSSEL EXTRACT

[75] Inventors: Takuo Kosuge; Kiyoshi Sugiyama, both of Shizuoka, Japan

[73] Assignees: James M. Broadbent, Victoria, Australia; Yoshiki Kosuge, Oshika, Japan

[21] Appl. No.: 829,656

[22] PCT Filed: Apr. 24, 1985

[86] PCT No.: PCT/AU85/00091
§ 371 Date: Jan. 23, 1986
§ 102(e) Date: Jan. 23, 1986

[87] PCT Pub. No.: WO85/05033
PCT Pub. Date: Nov. 21, 1985

[30] Foreign Application Priority Data

May 1, 1984 [AU] Australia ............................. PG4775

[51] Int. Cl.$^4$ ...................... A61K 35/12; A61K 33/14
[52] U.S. Cl. ..................................... 424/95; 424/153; 426/648; 426/654
[58] Field of Search .................. 248/153, 95; 426/648, 426/654

[56] References Cited

U.S. PATENT DOCUMENTS

| 4,341,774 | 7/1982 | Aoki et al. | 514/167 |
| 4,391,862 | 7/1983 | Suda et al. | 514/167 |
| 4,455,298 | 6/1984 | McFarlane et al. | 514/95 |
| 4,550,020 | 10/1985 | Rothman | 424/88 |
| 4,652,581 | 3/1987 | Fukawa et al. | 514/418 |
| 4,675,191 | 6/1987 | Villettaz | 426/10 |

Primary Examiner—John W. Rollins
Attorney, Agent, or Firm—Cushman, Darby & Cushman

[57] ABSTRACT

A method of stabilizing the activity of an extract of the New Zealand green lipped mussel (*Perna canaliculus*) includes adding at least one organic acid or an alkali metal or alkaline earth metal salt thereof to the extract. Preferred organic acids are organic aliphatic acids having from 1 to 10 carbon atoms, particularly tartaric acid. Also disclosed is a food supplement and/or pharmaceutical preparation which includes the stabilized extract.

13 Claims, No Drawings

STABILIZED MUSSEL EXTRACT

This invention relates to preparations and/or extracts of the New Zealand green lipped mussel (*Perna canaliculus*) and to the use thereof in food supplements and pharmaceutical preparations.

A mussel extract of this type is available on the market as a commercial product under the brand name "Seatone" and, since 1973, has been sold in pharmacies and health food stores in a number of countries, such as Canada, Australia, New Zealand, United Kingdom, Holland and Denmark. The substance is sold as a food supplement in the above countries.

A typical composition of the mussel extract "Seatone" named above is as follows:

moisture content: 0.65%–3.21% (average=2.23%)
lipid content: 0.67%–10.54% (average=9.09%)
protein content: 52.13%–55.60% (average=53.57%)
carbohydrate content: 18.60%–24.29% (average=22.25%)
ash content: 11.7%–14.90% (average=12.83%)

Minerals (averaged percentages)

sodium: 3.04%
potassium: 0.94%
magnesium: 0.41%
calcium: 0.49%
zinc: 0.01%
copper: 0.00062%
cadmium: 0.000027%
lead: 0.00016%
manganese: 0.00116%
iron: 0.04%
mercury: 0.0000196%
nickel: 0.0006%
selenium: 0.000145%

In terms of amino acids a typical composition of the product is as follows:

| Amino acids | % |
|---|---|
| Cysteic acid | 3,1 |
| Aspartic acid | 4,9 |
| Threonine | 2,3 |
| Serine | 2,0 |
| Glutamic acid | 6,4 |
| Proline | 2,2 |
| Glycine | 4,2 |
| Alanine | 2,4 |
| Valine | 1,9 |
| ½ Cystine | 0,6 |
| Methionine | 1,1 |
| Iso-Leucine | 1,8 |
| Tyrosine | 1,5 |
| Phenylalanine | 1,8 |
| NH$_4$ | 0,6 |
| Lysine | 3,2 |
| Histidine | 0,8 |
| Arginine | 3,5 |

"Seatone" and other similar extracts obtained from the mollusc *Perna canaliculus* have extremely low toxicity, and there has been no indication of any hazardous side effects and no contra-indication, apart from cases of persons being allergic to shellfish.

Extracts of *Perna canaliculus* have been reported to be of value in preventing, alleviating or treating gastro-intestinal irritation conditions, lesions, and/or ulcer formation, and more recently, there has been an increasing amount of interest in the use of these mussel extracts for the relief of arthritic symptoms. Evidence for an anti-inflammatory property of the New Zealand green lipped mussel is believed to have originated in the USA during the screening of marine molluscs for possible anti-tumour activities. A considerable amount of subjective clinical evidence has accumulated suggesting that the preparation may be of benefit in the treatment of arthritic disorders in men and animals. For example, in a preliminary therapeutic trial carried out in 86 patients, 55 with rheumatoid arthritis and 31 with osteoarthritis, the patients were treated for periods ranging from six months to 4.5 years: 67% of those with rheumatoid arthritis and 35% of those with osteoarthritis benefited. Toxic effects were uncommon and generally mild. Further investigations into the anti-inflammatory and anti-arthritic activity of these mussel extracts have been reported by T. E. Miller and D. Ormrod [The New Zealand Medical Journal, September 1980, No. 667, p. 187] and by R. G. Gibson, S. L. M. Gibson, V. Conway and D. Chappell [Practitioner, September 1980, Vol. 224, p. 955]. In the report of Miller et al, the anti-inflammatory effect of an extract when administered intraperitoneally is confirmed, however no anti-inflammatory effect was demonstrated after oral administration. Gibson et al have, however, shown in a double-blind clinical trial that the mussel extract sold as "Seatone", taken orally can be of benefit in rheumatoid arthritis and, to a lesser extent, osteoarthritis in man.

Arthritis in one or other of its several forms continues to be a major cause of disability around the world. Although many non-steroidal anti-inflammatory drugs are now available, none is wholly effective, and side effects remain a problem. The search for a safer and more effective anti-inflammatory agent therefore continues. As mentioned above, extracts of *Perna canaliculus* have extremely low toxicity and no hazardous side effects, and so the anti-inflammatory activity of such extracts could be of enormous benefit.

One major problem in investigating these extracts, however has been the fact that there has not been an effective pharmacological or bio-assay to express the activity of the mussel extracts. Yet another major problem has arisen from the loss of activity of these extracts on storage, such loss of activity possibly even giving rise to anomolous results in investigations into the activity of the extracts.

In Japanese Patent Application No. 58-142320 dated Aug. 3, 1983, in the name of J. Y. Kosuge, there is disclosed a method for assaying the activity of an extract of *Perna canaliculus* based on the suppression of bleeding. Further details of this assay method are set out below.

According to the present invention there is provided a method of stabilizing the activity of an extract of the New Zealand green lipped mussel (*Perna canaliculus*), which comprises adding at least one organic acid or an alkali metal or alkaline earth metal salt thereof to said extract.

In another aspect, this invention provides a food supplement and/or pharmaceutical preparation which comprises an extract of the New Zealand green lipped mussel (*Perna canaliculus*), and at least one organic acid or an alkali metal or alkaline earth metal salt thereof.

This invention allso provides a method of preventing, alleviating or treating gastro-intestinal irritation conditions, lesions, and/or ulcer formation, which comprises administration of an effective amount of stabilized extract of the New Zealand green lipped mussel as described above. This invention similarly provides a method of treatment of inflammatory and/or arthritic conditions which comprises administration of an effective amount of this stabilized extract.

The extract of *Perna canaliculus* as used in accordance with the present invention may be any product obtainable from the flesh of the mussel or its organs suitable for being used in the preparation of food supplements and/or pharmaceutical preparations. The extract may, for example, comprise the powder obtained by drying and grinding the whole of the flesh of the mollusc, or a powder obtained by drying and grinding the gonads of the mollusc. The preparations also include lipid extract mixtures obtained by solvent extraction of either of the powders mentioned above. The extract is preferably the extract sold commercially under the brand name "Seatone" which is prepared by the following process:

1. the outside of the shellfish is washed, for example by high pressure hosing,
2. the flesh is removed from the shell, for example, by hand, ensuring that no heat is applied, as the temperature should not exceed 10° C.,
3. the product is tested for bacteria and heavy metal content, as only shellfish which have no such contamination can be used,
4. the flesh is placed in a grinding machine and pulverized into small pieces, then placed onto trays, preferably having an uniform thickness, for example, of about ¾ inch,
5. the pieces are freeze-dried, and
6. the freeze-dried material is then crushed into a fine powder and sealed, preferably into vacuum-packed containers.

According to this invention, at least one organic acid or an alkaline metal or an alkaline earth metal salt thereof is added to the extract in order to stabilize the activity of the extract. Preferably, the organic acid is an organic aliphatic acid having, for example, from 1 to 10 carbon atoms. More preferably, the organic acid is a dibasic acid. Suitable acids which fall within the ambit of this invention and which are approved for use in food supplements and/or pharmaceutical preparations include acetic acid, citric acid, tartaric acid, succinic acid, lactic acid, gluconic acid, fumaric acid, sorbic acid, ascorbic acid, and oxalic acid. Particularly preferred is tartaric acid. Particularly preferred salts for use in accordance with the present invention are the sodium or potassium salts, for example sodium tartarate.

In addition to the organic acids added as stabilizers in accordance with the present invention, the food supplements and/or pharmaceutical preparations may also contain other components such as known preservatives and anti-oxidants.

Preferably, the food supplements and/or pharmaceutical preparations of this invention are provided in capsule form, with the stabilized extract in powder form enclosed in a gelatin capsule. These preparations may, however, be in other well known solid forms such as tablets or in liquid form such as in suspension. In all these forms, appropriate well known pharmaceutically acceptable carriers or diluents may be added to the stabilized extract.

The organic acid(s) or salts thereof may be added in amounts of from 0.1 to 0.2% by weight, as these amounts have also been found to be effective in stabilizing the mussel extract. Preferably, however, amounts of at least 2% by weight are used, and at present the most preferred amount is approximately 7% by weight.

Further details of the pharmacological assay method used in accordance with the present invention in determining the activity of the mussel extract, and of the stabilizing effect of this activity achieved in accordance with the present invention, are set out in greater detail below.

I. ASSAY PROCEDURE

Male mice weighing 20 g maintained under uniform conditions were used. The test material was homogenized in 1% methylcellulose-0.9% sodium chloride aqueous solution and administered intra-peritoneally. After ten minutes, each mouse was immobilised in a cage and the tail was cut at 2 cm from the end. Blood was collected from the cut tail over a predetermined period (usually one minute) and then haemolysed. Absorbance of the haemolysed blood, which varies with the volume collected, was determined spectroscopically at 540 nm.

In a similar manner, a control value was obtained from mice administered only 1% methylcellulose-0.9% sodium chloride aqueous solution. The suppression rate was calculated by the following equation:

$$\text{Suppression rate} = 100 \times \left(1 - \frac{\text{absorbance of sample}}{\text{absorbance of control}}\right)$$

The activity of the test material is expressed as mg of the sample for 50% suppression of bleeding [$ED_{50}$].

The following is an example of the assay procedure:

Four day male mice of weight 20 g were used. Each mouse was injected 1 ml of water suspension of 5 mg of mussel extract intra-peritoneally. Ten minutes after the injection, the tail was cut 2 cm from the end and dipped in 6 ml of 3.8% sodium citrate solution. The blood was collected for 1 minute. After haemolysis of the blood with 0.5% potassium cyanide solution, the blood volume was measured electrophotometrically.

Results are shown in the following Table:

| Group administered mussel extract | | Control | |
|---|---|---|---|
| Mouse No. | Absorbance | Mouse No. | Absorbance |
| 1 | 0.115 | 1 | 0.399 |
| 2 | 0.131 | 2 | 0.393 |
| 3 | 0.157 | 3 | 0.406 |
| 4 | 0.146 | 4 | 0.405 |
| Average | 0.137 | Average | 0.400 |

$$\text{Suppression rate (\%)} = 100 \left(1 - \frac{\text{absorbance of sample}}{\text{absorbance of control}}\right)$$
$$= 100 \left(1 - \frac{0.137}{0.400}\right) = 65.75\%$$

To confirm reliability of this pharmacological assay it needs to be correlated with other assays which have been recognized as assays for anti-inflammatory activity.

In an assay using a carrageenan-induced inflammatory oedema of the rat hind foot pad, as described in Miller et al (supra), 250 mg of mussel extract of 20 mg/kg $ED_{50}$ produced in a significant reduction (50%)

in the inflammatory response. 50 mg of mussel extract which was stabilized in accordance with this invention and had very high activity of 1.5 mg/kg $ED_{50}$ produced the same reduction in the inflammatory response, indicating that correlation exists between the assay methods.

II. STABILIZATION TESTS.

(a) Using the new pharmacological assay, the stability of the mussel extract was investigated. It was found that in the existing production of the mussel extract as described above, the activity decreased to one-third to one-fifth during production, especially in the freeze-drying stage. In order to prevent this loss of activity, the stability of the homogenised mussel flesh in aqueous suspension, was investigated. It was found that the suspension completely lost its activity after 2 hours at 30° C.

(b) The stabilizing effects of some common organic acids were investigated.

To suspensions of 12.5 mg of homogenized mussel flesh in 0.4 ml of saline, various amounts of organic acids were added and kept for 2 hours at 30° C. 0.4 ml of the resulting suspensions were injected into the peritoneal cavities of 20 g male mice. The bleeding suppression rate was measured by the assay procedure described above.

The results are shown in the following Table. Suppression rate of the suspension immediately after homogenization was 63%.

| Organic acid | mol | pH | Suppression rate % |
|---|---|---|---|
| acetic acid | 0.01 | 3.5 | 61 |
| citric acid | 0.002 | 3.3 | 35 |
| tartaric acid | 0.002 | 3.5 | 60 |
| succinic acid | 0.002 | 3.5 | 38 |
| lactic acid | 0.01 | 3.5 | 60 |
| control (without acids) | | | 0 |

As shown in the above table, each organic acid employed was effective to protect the suspension from loss of activity.

(c) In a further illustration of the stabilizing effect, 5 g of tartaric acid was added to 5 kg of the mussel flesh during mixing stage prior to freeze-drying. The mussel extract produced had an activity of 2.5 mg/kg, $ED_{50}$. This $ED_{50}$ value is about 5 times higher than the value for mussel extract provided without the acid stabilizer.

(d) Further studies were carried out to investigate the effect of pH on the stabilizing effect of tartaric and its salts. Various pHs were obtained by neutralization of tartaric acid by sodium hydroxide, and by sodium tartarate (pH 5.9). The results are shown in the following table:

| Test Solution | pH | Suppression rate % |
|---|---|---|
| 0.01 mol tartaric acid | 2.5 | 36 |
| 0.002 mol tartaric acid | 3.5 | 60 |
| 0.002 mol tartaric acid | 4.0 | 57 |
| 0.002 mol tartaric acid | 5.0 | 63 |
| 0.002 mol sodium tartarate | 5.9 | 75 |

In this example, 0.4 ml of test solution was added to a suspension of 12.5 mg of homogenized mussel flesh and kept for 2 hours at 30° C.

The suspension was injected intra-peritoneally to mice, and the bleeding suppression rate was determined as previously described.

(e) In a further illustrative example, 7 g of sodium tartarate was added to 5 kg of the mussel flesh in a mixing stage prior to freeze-drying. The mussel extract produced had an activity of 1.7 mg/kg $ED_{50}$ which is higher than the activity obtained by use of tartaric acid (see (c) above).

(f) A further example shows use of differing amounts of organic acid as stabilizer. To a suspension of 12.5 mg of homogenized mussel flesh 0.025 mg tartaric acid solution and 0.005 mg tartaric acid solution were added, respectively, and kept for 2 hours at 30° C. 0.4 ml of each suspension was injected intra-peritoneally to male mice (20 g), and the bleeding suppression rates were 65% and 39% respectively. (0.002 mol tartaric acid solution corresponds to 0.012 mg tartaric acid in 0.4 ml of water.)

(g) The stabilizing effect of the additive of this invention over various periods of time was investigated with a view to ascertaining the amount of additive preferred for commercial production. In these tests, the amount of additive needed to prevent 50% loss of activity of homogenized mussel flesh over a prticular period of time, was determined as follows:

| Amount of additive (tartic acid % by weight) | Activity Data |
|---|---|
| 0 | 50% activity lost over 24 hrs |
| 2 | 50% activity lost over 7 days |
| 7 | 50% activity lost over 1 month |
| 30 | 50% activity lost over 3 months |

It will be seen from the above that whilst an amount of 2% of additive is sufficient to stabilize the mussel flesh during and immediately after production (7 days), for commercial purposes an amount of at least 7% of additive provides stabilization for longer periods (1 month or more).

It will be appreciated that the above specific examples are given by way of illustration of this invention, and that variations and modifications may be made thereto without departing from the spirit and scope of the present invention as broadly described herein.

We claim:

1. A method of stabilizing the activity of an extract of the New Zealand green lipped mussel (*Perna canaliculus*), which comprises adding at least one organic aliphatic acid having from 1 to 10 carbon atoms or an alkali metal or alkaline earth metal salt thereof to said extract.

2. A method according to claim 1, wherein the organic acid is selected from the group consisting of acetic acid, citric acid, tartaric acid, succinic acid, lactic acid, gluconic acid, fumaric acid, sorbic acid, ascorbic acid, and oxalic acid.

3. A method according to claim 1 wherein tartaric acid or an alkali metal or alkaline earth metal salt thereof is added to said extract.

4. A method according to claim 1, wherein said organic acid or salt thereof is added in an amount of at least 2% by weight of said extract.

5. A method according to claim 4, wherein said organic acid or salt thereof is added in an amount of approximately 7% by weight of said extract.

6. A food supplement which comprises an extract of the New Zealand green lipped mussel (*Perna canaliculus*), and at least one organic aliphatic acid having from 1 to 10 carbon atoms or an alkali metal or alkaline earth metal salt thereof.

7. A food supplement according to claim 6, wherein the organic acid is selected from the group consisting of acetic acid, citric acid, tartaric acid, succinic acid, lactic acid, gluconic acid, fumaric acid, sorbic acid, ascorbic acid, and oxalic acid.

8. A food supplement according to claim 6, wherein said organic acid or salt thereof is tartaric acid or an alkali metal or alkaline earth metal salt thereof.

9. A food supplement according to claim 6, wherein said organic acid in salt thereof comprises an amount of at least 2% by weight of said extract.

10. A food supplement according to claim 9, wherein said organic acid or salt thereof comprises an amount of approximately 7% by weight of said extract.

11. A food supplement according to claim 6, wherein said extract is obtained by freeze-drying the flesh of the mussel.

12. A method of stabilizing an extract of the New Zealand green lipped mussel (*Perna canaliculus*) against loss of activity with time comprising adding to the extract a stabilizing-effective amount of at least one aliphatic acid having from 1 to 10 carbon atoms or an alkali metal or alkaline earth metal salt thereof to the extract.

13. A food supplement comprising an extract of the New Zealand green lipped mussel (*Perna canaliculus*) stabilized against loss of activity with time by the addition thereto of a stabilizing amount of at least one aliphatic acid having from 1 to 10 carbon atoms or an alkali metal or alkaline earth metal salt thereof.

* * * * *